US007807628B2

(12) United States Patent
Murakami et al.

(10) Patent No.: US 7,807,628 B2
(45) Date of Patent: Oct. 5, 2010

(54) THERAPEUTIC AGENT FOR DENTIN-PULP COMPLEX REGENERATION

(75) Inventors: Shinya Murakami, Suita (JP); Yoshio Shimabukuro, Suita (JP)

(73) Assignees: Osaka University, Osaka (JP); Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/083,734

(22) PCT Filed: Oct. 19, 2006

(86) PCT No.: PCT/JP2006/321308

§ 371 (c)(1), (2), (4) Date: Jul. 1, 2008

(87) PCT Pub. No.: WO2007/046540

PCT Pub. Date: Apr. 26, 2007

(65) Prior Publication Data

US 2009/0118179 A1 May 7, 2009

(30) Foreign Application Priority Data

Oct. 19, 2005 (JP) ............................ 2005-305076

(51) Int. Cl.
*A61K 38/18* (2006.01)
*C07K 14/50* (2006.01)

(52) U.S. Cl. ............................ 514/2; 514/12; 530/399

(58) Field of Classification Search ...................... None
See application file for complete search history.

(56) References Cited

U.S. PATENT DOCUMENTS

| | | | | |
|---|---|---|---|---|
| 6,046,164 | A | 4/2000 | Asano et al. | |
| 6,831,058 | B1 | 12/2004 | Ikada et al. | |
| 2005/0142076 | A1* | 6/2005 | Fukunaga et al. | 424/50 |

FOREIGN PATENT DOCUMENTS

| | | |
|---|---|---|
| EP | 0 702 959 | 3/1996 |
| EP | 1 498 135 | 1/2005 |
| JP | 6-340555 | 12/1994 |
| JP | 7-17876 | 1/1995 |
| WO | 94/27630 | 12/1994 |
| WO | 03/082321 | 10/2003 |

OTHER PUBLICATIONS

Roberts-Clark et al. Arch. Oral Biol. 45: 1013-1016, 2000.*

M. Nakashima, "*The effects of growth factors on DNA synthesis, proteoglycan synthesis and alkaline phosphatase activity in bovine dental pulp cells*", Archs Oral Biol. vol. 37, No. 3, pp. 231-236 (1992).

Kazuhisa Nakao et al., "*FGF-2 potently induces both proliferation and DSP expression in collagen type I gel cultures of adult incisor immature pulp cells*", Biochemical and Biophysical Research Communications, vol. 325, pp. 1052-1059 (2004).

Toshihiko Takase, "*A Histopathological Study of α-tricalcium Phosphate Cement Containing Growth Factor as Direct Pulp Capping Agent*", Dept. of Endodontics, Nihon University School of Dentistry at Matsudo, vol. 25, pp. 415-426 (1999)—English language abstract at p. 426.

Supplementary European Search Report issued Aug. 27, 2009 in corresponding European Patent Application No. 06 82 2285.

Kadokura, H. "*Effects of Basic FGF on Differentiation of Odontoblast-like Cells in Rat Dental Pulp Cells*", Japanese Journal of Conservative Dentistry, Nihon Shika Hozon Gakkai, Tokyo, JP, vol. 45, No. 1, Jan. 1, 2002, pp. 106-118, XP003012053.

Hu et al. "*Reparative Dentin Formation in Rat Molars after Direct Pulp Capping with Growth Factors*", Journal of Endodontics, Lippincott, Williams & Williams, Philadelphia, PA, US, vol. 24, No. 11, Nov. 1, 1998, pp. 744-751, XP022196217.

Tziafas, D. et al. "*Effects of Recombinant Basic Fibroblast Growth Factor, Insulin-like Growth Factor-II, and Transforming Growth Factor—$\beta_1$ on Dog Dental Pulp Cells in Vivo*", Archives of Oral Biology, vol. 43, No. 6, Jun. 1998, pp. 431-444, XP002540239.

Shiba, Hideki et al. "*Effects of Basic Fibroblast Growth Factor on Proliferation, the Expression of Osteonection (SPARC) and Alkaline Phosphatase, and Calcification in Cultures of Human Pulp Cells*", Developmental Biology, vol. 170, No. 2, 1995, pp. 457-466, XP002540240.

* cited by examiner

*Primary Examiner*—Christine J Saoud
(74) *Attorney, Agent, or Firm*—Wenderoth, Lind & Ponack, L.L.P.

(57) ABSTRACT

The present invention provides a therapeutic agent for regenerating a dentin-pulp complex, containing a basic fibroblast growth factor and/or a homolog thereof as an active ingredient. The present invention also provides a pulp-capping agent containing a basic fibroblast growth factor and/or a homolog thereof as an active ingredient.

14 Claims, 5 Drawing Sheets

(A)

(B)

(C)

(D)

THERAPEUTIC AGENT FOR DENTIN-PULP COMPLEX REGENERATION

This application is the U.S. National Stage of International Application No. PCT/JP2006/321308, filed Oct. 19, 2006.

TECHNICAL FIELD

The present invention relates to a therapeutic agent for regenerating a dentin-pulp complex that can be utilized for pulp-conservative therapy of a tooth with advanced dental caries and the like.

BACKGROUND ART

Dental caries is an infectious disease caused by oral acid-producing bacteria such as *Streptococcus mutans* and *Streptococcus sobrinus*, characterized by dental parenchyma loss due to an imbalance between decalcification and recalcification. In a currently available therapeutic method for teeth with dental caries that reached the dentin as well as pulp, a calcium hydroxide preparation is applied as a pulp-capping agent to the exposed pulp, and thereafter dental cement and the like are filled. However, in this method, a necrotic layer occurs on the pulp face in contact with calcium hydroxide, and the damaged pulp tissue never regenerates, with only slight formation of tertiary dentin under the necrotic layer.

Both dentin and pulp are tissues derived from mesenchymal stem cells, but they were in the past considered different tissues, the former as hard tissue, and the latter as soft tissue. Recent studies have recognized them as an embryologically and functionally integrated tissue, called "a dentin-pulp complex". Odontoblasts in pulp are known to extend their processes into dentinal tubules, and to play a role as a sensor for exogenous stimuli; the physiological morphology and function of the dentin-pulp complex are deeply involved in the survival of a tooth. For this reason, the prognosis with the above-described currently available therapy is not good at all.

Basic fibroblast growth factor (hereinafter sometimes abbreviated bFGF) is a peptidic cell growth factor confirmed to be present in the pituitary, brain, retina, corpus luteum, adrenal, kidney, placenta, prostate, thymus, chondrosarcoma, and macrophage ("Saibou Seicho Inshi Part II", edited by the Japanese Tissue Culture Association, Asakura Shoten, 1987, p. 15-20). Basic fibroblast growth factor was initially named for its potent proliferative action on fibroblasts such as BALB/c3T3 cells (D. Gospodarowicz, Nature, vol. 249, p. 123 (1974)), but was later shown to promote the proliferation of most mesodermal cells, particularly of vascular endothelial cells (D. Gospodarowicz, National Cancer Institute Monograph, vol. 48, p. 109 (1978)), and to promote the proliferation of satellite cells of skeletal muscle (R. E. Allen, Experimental Cell Research, vol. 152, p. 154 (1984)). In recent years, there have been clinical applications of basic fibroblast growth factor in wound treatment, and applications of basic fibroblast growth factor for repairing blood vessel based on angiogenic action and the like.

Basic fibroblast growth factor has been reported to induce the proliferation of pulp cells and have a regulatory action on the differentiation of pulp cells into odontoblasts in vitro (M. Nakashima, Archs Oral Biol., vol. 37 (3), p. 231-236 (1992) and K. Nakao, Biochem Biophys Res Commun, vol. 325, p. 1052-1059 (2004)); it has been reported that TGF-β1 has a significant effect on the formation of repaired dentin, with no effect of basic fibroblast growth factor observed in vivo (D. Tziafas, Archs Oral Biol., vol. 43, p. 431-444 (1998) and C.-C. Hu, J. Endodontics, vol. 24(11), p. 744-751 (1998)).

For example, described as a basic fibroblast growth factor preparation in WO94/27630 is a crosslinked gelatin gel preparation containing basic fibroblast growth factor, useful for the treatment of bone disease; JP-A-7-233085 states that basic fibroblast growth factor and/or a homolog thereof possesses an excellent promoting effect on neogenesis or regeneration of cartilage tissue, and is useful for repair of cartilage tissue. JP-A-7-17876 discloses a therapeutic agent of periodontal disease comprising basic fibroblast growth factor and/or a homolog thereof. Furthermore, WO03/082321 discloses a viscous preparation for dental use comprising basic fibroblast growth factor, useful for the treatment of periodontal disease. The therapeutic agent of periodontal disease disclosed in JP-A-7-17876 is expected to find an application for the regeneration of dentin lost by dental caries (paragraph [0035] in the description of JP-A-7-17876). However, JP-A-7-17876 gives no disclosure or suggestion concerning the treatment of dental parenchyma loss due to dental caries caused by acid-producing bacteria such as *Streptococcus mutans*, tooth attrition or injury; there is a demand for the development of a therapeutic agent capable of radically treating dental parenchyma loss due to dental caries caused by acid-producing bacteria, tooth attrition or injury.

DISCLOSURE OF THE INVENTION

It is an object of the present invention to provide a drug capable of acting on undifferentiated mesenchymal stem cells and odontoblasts that are present in pulp tissue to positively reconstruct a dentin-pulp complex.

The present inventors diligently investigated in view of the above-described problems, found that by administering basic fibroblast growth factor to a defect in a dentin-pulp complex or dentin due to dental caries and the like, not only the proliferation of pulp cells is induced and pulp tissue is regenerated, but also the proliferation and differentiation induction of odontoblasts are activated, and that dentin is newly produced, whereby the dentin-pulp complex having the intrinsic function is reconstructed, and developed the present invention.

Accordingly, the present invention provides the following:

[1] A therapeutic agent for regenerating a dentin-pulp complex, comprising basic fibroblast growth factor and/or a homolog thereof as an active ingredient,

[2] the therapeutic agent according to [1] above, wherein the basic fibroblast growth factor is human basic fibroblast growth factor,

[3] the therapeutic agent according to [1] above, further comprising a carrier,

[4] the therapeutic agent according to [3] above, wherein the carrier is hydroxypropylcellulose or crosslinked gelatin gel,

[5] the therapeutic agent according to any one of [1] to [4] above, which is for use in the treatment of a tooth with a dental parenchyma loss due to dental caries, tooth attrition or injury,

[6] the therapeutic agent according to [5] above, wherein the dental caries has reached the pulp,

[7] a use of basic fibroblast growth factor and/or a homolog thereof for producing the therapeutic agent according to any one of [1] to [6] above,

[8] a commercial package comprising the therapeutic agent according to any one of [1] to [6] above, and a written matter associated therewith, the written matter stating that the therapeutic agent can or should be used, for the treatment of regenerating the dentin-pulp complex,

[9] a method of regenerating a dentin-pulp complex, comprising a step for administering the therapeutic agent according to any one of [1] to [6] above to a subject in need thereof,

[10] a pulp-capping agent comprising basic fibroblast growth factor and/or a homolog thereof as an active ingredient,

[11] a use of basic fibroblast growth factor and/or a homolog thereof for producing the pulp-capping agent according to [10] above,

[12] a commercial package comprising the pulp-capping agent according to [10] above and a written matter associated therewith, the written matter stating that the pulp-capping agent can or should be used, for direct or indirect pulp capping, and

[13] a method of capping pulp directly or indirectly, comprising a step for administering the pulp-capping agent according to [10] above to a subject in need thereof.

BEST MODE FOR CARRYING OUT THE INVENTION

Figure 1:
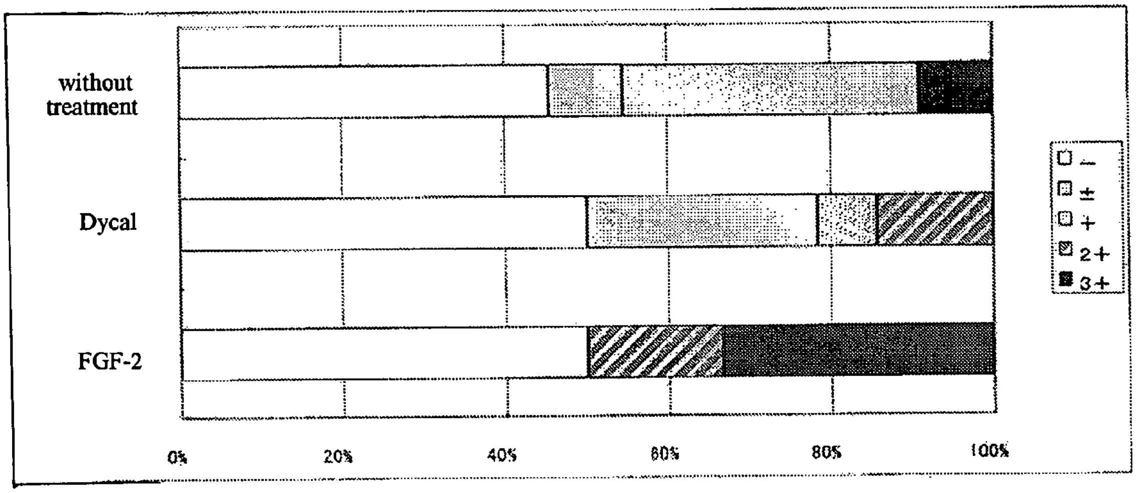
FIG. 1 is a graph showing the effects of bFGF on dentinogenesis. −: No tertiary dentin formed, ±: almost no tertiary dentin formed, +: a small amount of tertiary dentin formed, 2+: a moderate amount of tertiary dentin formed, 3+: tertiary dentin formed remarkably.
Figure 2:
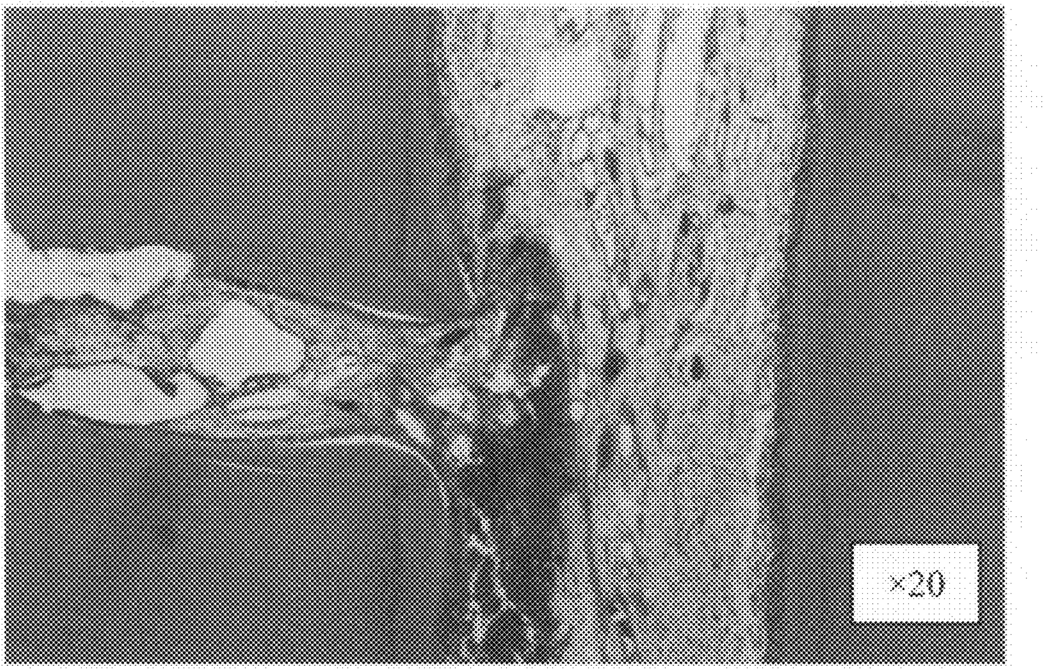
FIG. 2(A)-2(D) shows light photomicrographs of (A) a specimen without treatment, (B) a specimen treated with crosslinked gelatin gel alone, (C) a specimen treated with bFGF, and (D) a specimen treated with Dycal, after HE staining, in a regeneration test for the dentin-pulp complex after pulp exposure surgery on a dog.
Figure 2:
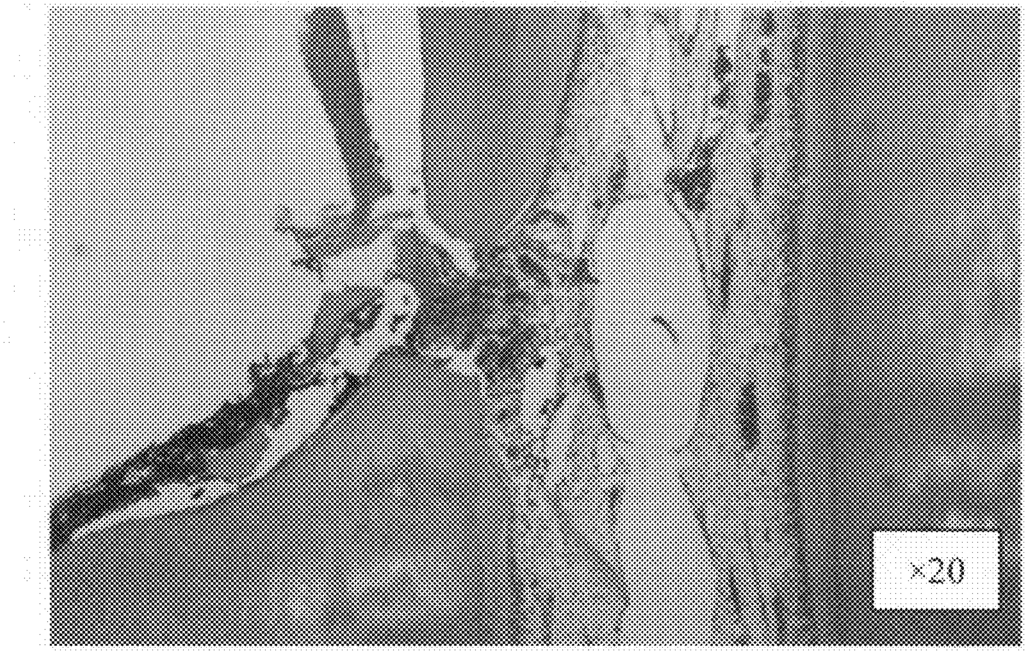
Figure 2:
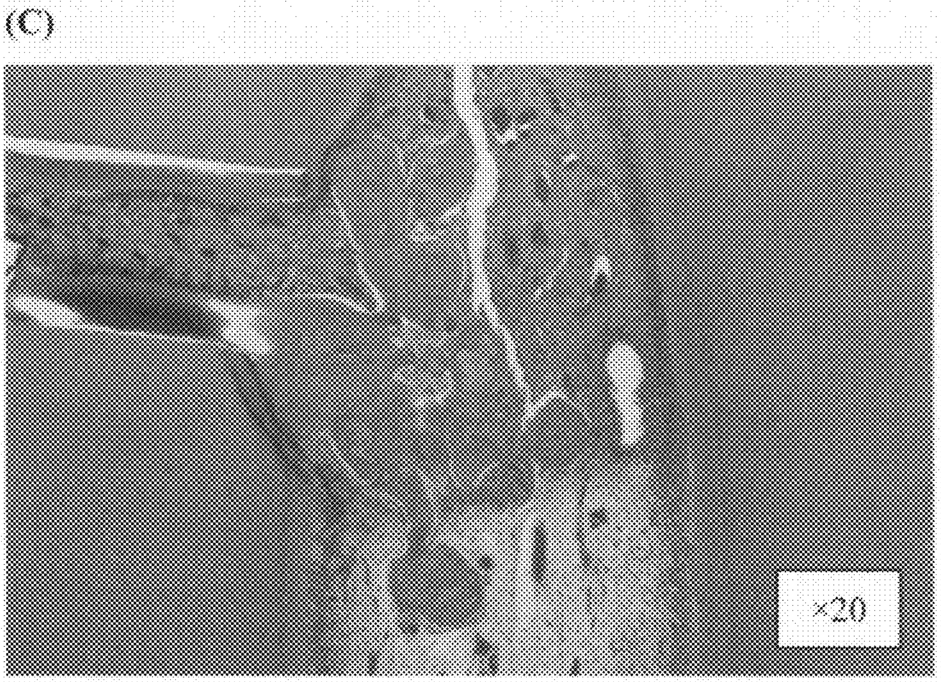
Figure 2:
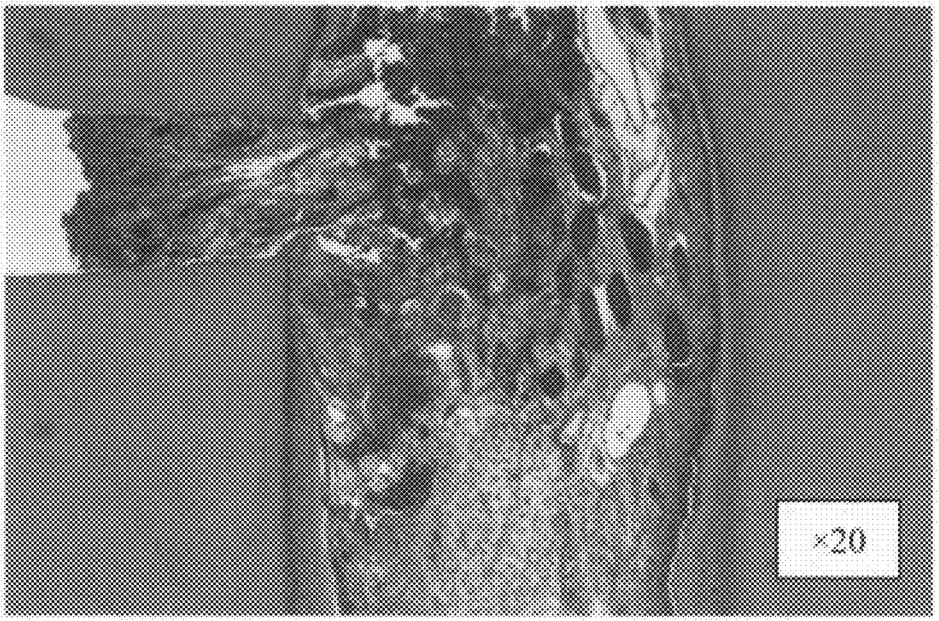

The present invention provides a therapeutic agent for regenerating a dentin-pulp complex, comprising basic fibroblast growth factor and/or a homolog thereof as an active ingredient.

In the present invention, the dentin-pulp complex refers to a composite structure composed of pulp tissue capable of producing dentin and dentin including the pulp tissue, which is taken as a single functional unit.

In the present invention, "regenerative treatment" refers to a form of treatment accompanied by the regeneration of dentin-pulp complex lost by dental caries or tooth attrition.

Basic fibroblast growth factor (bFGF or FGF-2: hereinafter abbreviated as bFGF) and a homolog thereof are obtained by isolation and purification of a naturally occurring product or a product of a microorganism or cultured cells by genetic engineering, or by chemical or biological modification thereof.

Natural bFGF is exemplified by those derived from mammals. Mammals include human, monkey, dog, pig, sheep, cattle, horse and the like. bFGF can be obtained from these mammals by a commonly known method, and commercially available ones can also be used. The bFGF used in the present invention is particularly preferably human bFGF or a homolog thereof.

In the regenerative therapeutic agent of the present invention, a homolog of bFGF may be used as an active ingredient. Here, a homolog of bFGF means the polypeptide of [I] or [II] below:

[I] A polypeptide consisting of substantially the same amino acid sequence as bFGF produced in a particular mammal. Substantially same amino acid sequence means an amino acid sequence having 1 to 6 amino acids substituted by different kind(s) of amino acids, and having the biological activity of bFGF.

[II] A polypeptide wherein an additional amino acid segment is added to the N-terminal and/or C-terminal of bFGF produced by a particular mammal, or to the N-terminal and/or C-terminal of the polypeptide of [I] above. The additional amino acid segment means one that consists of 1 to 12 amino acids, and that does not impair the biological activity of bFGF or the biological activity of the polypeptide of [I] above.

Human bFGF is a polypeptide consisting of 146 amino acids; in the regenerative therapeutic agent of the present invention, as a homolog of human bFGF (the homolog of [I] above), for example, the polypeptide consisting of 146 amino acids described in JP-A-2-504468 may be used. In this polypeptide, the 69-position cysteine (Cys) and 87-position cysteine (Cys) constituting the amino acid sequence of human bFGF are respectively substituted by serine (Ser).

As the homolog of [II] above, for example, a polypeptide consisting of 155 amino acids described in JP-A-63-500843 may be used. In this polypeptide, a segment consisting of 9 amino acids is added to the N-terminal of human bFGF.

A polypeptide consisting of 147 amino acids wherein methionine (Met) is added to the N-terminal and a polypeptide consisting of 157 amino acids described in JP-A-63-501953, wherein a segment consisting of 11 amino acids is added to the N-terminal may be used.

A particularly preferable bFGF is trafermin (genetic recombinant).

In the regenerative therapeutic agent of the present invention, one kind of bFGF may be used alone, and a plural kinds thereof may be used in combination. Furthermore, as described above, while the homolog of bFGF includes plural kinds, such homologs may also be used alone, or in combination.

Since the residual amount of bFGF in living organisms is an ultratrace amount, from the viewpoint of commercially stable supply of the regenerative therapeutic agent of the present invention, that bFGF produced by a microorganism such as *Escherichia coli* or produced in cultured cells by genetic engineering or a homolog thereof is particularly preferably used. When a gene for producing bFGF or a homolog thereof (in this case, generally the polypeptide of [I] above) is incorporated into a microorganism or cultured cells, the product from this microorganism or cultured cells is generally a polypeptide wherein an additional amino acid segment is added to the N-terminal and/or C-terminal of bFGF, or to the N-terminal and/or C-terminal of the polypeptide of [I] above, that is, the polypeptide of [II] described above.

The regenerative therapeutic agent of the present invention can be prepared as a viscous preparation, gelling agent, liquids, ointments, emulsions, infusions, plasters, injections, powders and the like, by combining bFGF and/or a homolog thereof with a pharmaceutically acceptable carrier, for example, a solvent, isotonizing agent, emulsifier, suspending agent, stabilizer, thickener, filling agent for dental use and the like by ordinary preparation technology. Furthermore, the regenerative therapeutic agent of the present invention can also be used in combination with a scaffold. As the regenerative therapeutic agent of the present invention, specifically, viscous preparations and gelling agents can be mentioned as suitable. Hereinafter, each case is described in detail.

When the regenerative therapeutic agent of the present invention is a viscous preparation (hereinafter also referred to as the viscous preparation of the present invention), the concentration of bFGF and/or a homolog thereof contained in the viscous preparation of the present invention is not particularly limited, as long as the regeneration of the dentin-pulp complex is induced, and the concentration is, for example, generally 0.0001 to 20% by weight, preferably 0.001 to 10% by weight, more preferably 0.01 to 1% by weight, still more preferably 0.05 to 0.5% by weight based on the total weight of the viscous preparation.

The viscous preparation of the present invention is preferably a preparation that shows a viscosity of about 20 to 25,000 mPa·s, more preferably, about 1,000 to 20,000 mPa·s, particularly preferably about 3,000 to 15,000 mPa·s, as determined at 25° C. using an E type viscometer. The viscosity is preferably in this range from the viewpoint of local retention after administration.

An adjustment of the viscosity can be achieved usually by the addition of a thickener.

As the thickener, any optional materials can be used with an optional concentration so long as it is capable of showing, for example, a viscosity in the above-described range (about 20 to 25,000 mPa·s) when prepared as a solution, does not adversely influence the stability of bFGF, and is pharmaceutically acceptable. Specifically, hydroxypropyl cellulose, sodium alginate, propyleneglycol alginate, carboxyvinyl polymer, carmellose sodium, hyarulonic acid, sodium hyarulonate, hydroxyethyl cellulose, hydroxyethylmethyl cellulose, hydroxypropylmethyl cellulose, polyacrylic acid, sodium polyacrylate, polyacrylic acid partially neutralized product, polyvinyl alcohol, methyl cellulose, xanthan gum, chondroitin acid, and sodium chondroitin sulfate and the like can be used. In particular, considering the effect on the stability of bFGF, hydroxypropyl cellulose (HPC), sodium hyarulonate, xanthan gum, and sodium chondroitin sulfate can preferably be used, and particularly, hydroxypropyl cellulose can preferably be used.

In addition to these thickeners, thickeners such as gum arabic, gum arabic powder, guar gum, glucono-δ-lactone, gelatin, dextran 70, dextrin, tragacanth, tragacanth powder, povidone, starch syrup, rosin, polyoxyethylene (160) polyoxypropylene (30) glycol, polyoxyethylene (200) polyoxypropylene glycol (70), and a copolymer of methyl vinyl ether and maleic anhydride can also be used.

The viscous preparation of the present invention can be prepared by, for example, a method described in WO03/082321.

The aforementioned hydroxypropylcellulose (HPC) is preferably a hydroxypropyl ether derivative of cellulose, preferred are those containing 53.4 to 77.5% of a hydroxypropyl group when a dried material is determined (Japanese Pharmacopoeia Fourteenth Edition D). When HPC is dissolved in water, it becomes a viscous liquid, any HPC with an optionally chosen molecular weight showing a viscosity of about 20 to 25,000 mPa·s as determined at 25° C. using an E type viscometer when prepared as an aqueous solution, can be used at concentrations that produce a viscosity in the above-described range. However, one having a molecular weight of about 100,000 to 500,000, which shows high thickening property with a low concentration, can preferably be used, and one having a molecular weight of about 110,000 to 400,000 is more preferable. For example, when HPC with a molecular weight of about 110,000 to 150,000 is used, HPC-M produced by Nippon Soda Co., Ltd. can be used preferably with a ratio of about 2 to 18% by weight, more preferably about 3 to 10% by weight based on the whole viscous preparation of the present invention. When HPC with a molecular weight of about 250,000 to 400,000 is used, HPC-H produced by Nippon Soda Co., Ltd. can be used preferably with a ratio of about 1 to 9% by weight, more preferably about 2 to 6% by weight based on the whole viscous preparation of the present invention. As long as a viscosity in the above-described range can be accomplished, HPCs with different molecular weights can also be used in mixture as appropriate.

The viscous preparation of the present invention can be prepared by mixing the above-described thickener in bFGF and/or a homolog thereof, and dissolving the mixture in a dissolving solution to obtain a solution having a predetermined viscosity. The ratio of bFGF and/or a homolog thereof based on the whole viscous preparation of the present invention is 0.0001 to 20% by weight, as described above; to obtain such a ratio, bFGF and/or a homolog thereof is mixed. As the dissolving solution, water can preferably be used. A ratio of the thickener to be used based on the whole viscous preparation of the present invention varies depending on the kind of thickener used, and can be determined within the range that shows a viscosity of about 20 to 25,000 mPa·s (E type viscometer) in solution. For example, when a HPC having a molecular weight of about 110,000 to 150,000 is used as the thickener, the thickener is dissolved in a dissolving solution to obtain a ratio of about 2 to 18% by weight, preferably a ratio of about 3 to 10% by weight. When an HPC having a molecular weight of about 250,000 to 400,000 is used, the thickener is dissolved in a dissolving solution to obtain a ratio of about 1 to 9% by weight, preferably a ratio of about 2 to 6% by weight.

If the regenerative therapeutic agent of the present invention is a gelling agent (hereinafter also referred to as the gelling agent of the present invention), the gelling agent of the present invention preferably contains gelatin as a carrier.

Since the aforementioned gelatin is a natural polymer that is degradable and absorbable in living organisms, has excellent biocompatibility, and is minimally irritant to living organisms, it is also preferably as a sustained-release carrier. Gelatin is generally water-soluble and hence is preferably insolubilized. Specifically, crosslinked gelatin gel prepared by water-insolubilizing gelatin by crosslinking treatment can preferably be used.

The gelatin serving as the raw material for crosslinked gelatin gel is not particularly limited, and may be a commonly available one. Examples of such gelatin include alkali-treated gelatin having an isoelectric point of nearly 5 (acidic gelatin), acid-treated gelatin having an isoelectric point of nearly 9 (alkali gelatin) and the like, and acidic gelatin having an isoelectric point of nearly 5 is preferable from the viewpoint of affinity for bFGF. Although one kind of gelatin may be used, different kinds of different raw materials and properties such as solubility, molecular weight, and isoelectric point may be used in mixture as appropriate.

The crosslinking agent for gelatin is not particularly limited, as long as the toxicity thereof to living organisms is low; for example, glutaraldehyde, water-soluble carbodiimides such as 1-ethyl-3-(3-dimethylaminopropyl)carbodiimide hydrochloride and 1-cyclohexyl-3-(2-morpholinoethyl)carbodiimide-metho-p-toluenesulfonate, bisepoxy compounds, formalin and the like are preferable; glutaraldehyde and 1-ethyl-3-(3-dimethylaminopropyl)carbodiimide hydrochloride are particularly preferable.

Gelatin may be crosslinked by heat treatment or ultraviolet light irradiation or electron beam irradiation.

When the carrier is crosslinked gelatin, the gelling agent of the present invention can be prepared by, for example, a method described in WO94/27630.

The form of the crosslinked gelatin gel used in the gelling agent of the present invention is not particularly limited; for example, columnar form, prismatic form, sheet-like form, disc-like form, spherical form, particulate form, granular form, pasty form and the like can be mentioned. When the crosslinked gelatin gel is used as an injectable preparation, a spherical, particulate, granular, or pasty one is preferable.

Columnar, prismatic, sheet-like, or disc-like crosslinked gelatin gel can be prepared by adding an aqueous solution of a crosslinking agent to an aqueous solution of gelatin, or adding gelatin to an aqueous solution of a crosslinking agent, casting the mixture into a mold having a desired form, and allowing a crosslinking reaction. A molded gelatin gel may be used as it is, or an aqueous solution of a crosslinking agent may be added after drying. For quenching the crosslinking reaction, the gel may be brought into contact with a low-molecular substance having an amino group, such as ethanolamine or glycine, or an aqueous solution having a pH of not more than 2.5 is added. The obtained crosslinked gelatin gel is washed with distilled water, ethanol, 2-propanol (hereinafter, referred to as IPA), acetone and the like, and subjected to the formulation of a gelling agent.

The water content of the obtained crosslinked gelatin gel is 50 to 99 w/w %. Here, the water content of the gel refers to the ratio of the weight of water in the gel, relative to the total weight of the gel in a wet state.

Pasty crosslinked gelatin gel can be prepared by a method similar to the above-described method of preparing a columnar, prismatic, sheet-like, or disc-like crosslinked gelatin gel.

Crosslinking reaction conditions are to be chosen as appropriate; reaction temperature is preferably 0 to 40° C., and reaction time is preferably 1 to 48 hours.

The thus-obtained crosslinked gelatin gel can also be dried under reduced pressure or freeze-dried.

Freeze-drying is performed by, for example, placing the crosslinked gelatin gel in distilled water, and freezing the gel in liquid nitrogen for not less than 30 minutes or at −80° C. for not less than 1 hour, and then drying the gel in a freeze-dryer for 1 to 3 days.

The concentrations of gelatin and crosslinking agent for preparing crosslinked gelatin gel are to be chosen according to desired water content as appropriate; a gelatin concentration of 1 to 100 w/v % and a crosslinking agent concentration of 0.01 to 100 w/v % (equivalent to 1 to 5400 mM) are preferable.

Crosslinked gelatin gel can be made to have a desired water content by changing the concentrations of gelatin (raw materials) and crosslinking agent. When the water content is increased, both the gelatin concentration and the crosslinking agent concentration may be reduced; when the water content is decreased, both the gelatin concentration and the crosslinking agent concentration may be increased.

To carry bFGF on the thus-prepared crosslinked gelatin gel, an aqueous solution of bFGF is added dropwise to the crosslinked gelatin gel to cause impregnation, or the crosslinked gelatin gel is suspended in an aqueous solution of bFGF, to cause re-swelling.

The amount of bFGF that can be carried on the crosslinked gelatin gel varies depending on the water content and the like of the crosslinked gelatin gel, and can be 0.1 to 500 μg per 1 mg of the crosslinked gelatin gel.

Duration of sustained release, the amount of bFGF released and the like vary depending on a variety of conditions such as the water content of crosslinked gelatin gel, the physical property of the gelatin used, such as isoelectric point and the like, the amount of bFGF carried in the preparation, and the site of administration and the like.

The gelling agent of the present invention thus obtained can also be freeze-dried. For freeze-drying, for example, the gelling agent is frozen in liquid nitrogen for not less than 30 minutes or at −80° C. for not less than 1 hour, and then dried in a freeze-dryer for 1 to 3 days.

When the gelling agent of the present invention is prepared as an injectable preparation, the gelling agent is suspended in a medium such as purified water for injection, physiological saline, or a buffer solution as appropriate. The buffer solution is exemplified by phosphate buffer solutions, acetate buffer solutions, citrate buffer solutions and the like. Where necessary, dispersing agents, surfactants, isotonizing agents, pH adjusters, soothing agents, stabilizers, preservatives, coloring agents and the like, which are generally used for the production of an injectable preparation, can be added as appropriate.

As a carrier is contained in the regenerative therapeutic agent of the present invention, bFGF and/or a homolog thereof is stably retained, making it possible to apply bFGF and/or a homolog thereof at low contents constantly and uniformly, and to obtain a preparation showing excellent local retention.

The regenerative therapeutic agent of the present invention has an excellent regenerating action on the dentin-pulp complex, and can suitably be used for the treatment of a tooth with a dental parenchyma loss due to dental caries, tooth attrition or injury and the like, particularly a tooth with severe dental caries that reached the pulp. The regenerative therapeutic agent of the present invention is also applicable to regenerative treatment of the dentin-pulp complex, not only in human, but also in other mammals (for example, mouse, rat, hamster, rabbit, cat, dog, cattle, sheep, monkey and the like).

The dentin-pulp complex regenerated by the regenerative therapeutic agent of the present invention has morphology more similar to the physiological morphology than a dentin-pulp treated with conventional drugs such as calcium hydroxide preparations and the like. It is preferable that the dentin-pulp complex regenerated by the regenerative therapeutic agent of the present invention has a function more similar to the physiological function than a dentin-pulp treated with conventional drugs such as calcium hydroxide preparations and the like.

"The physiological morphology" refers to the form possessed by the intrinsic dentin-pulp complex. Specifically, the dentin-pulp complex regenerated by the regenerative therapeutic agent of the present invention is a complex wherein dentin is located on the dental caries cavity side, and pulp is located on the intrinsic pulp side, with odontoblast processes extending toward dentin. "The physiological function" refers to the function possessed by the intrinsic dentin-pulp complex. Specifically, this is the function to line enamel to configure a tooth that endures occlusal force, and to serve as a sensory organ for mechanical stimulation or chemical stimulation exerted on a tooth in dental caries and tooth attrition. In the intrinsic dentin-pulp complex, odontoblasts in the pulp are known to extend their processes into dentinal tubules, and to play a role as a sensor for extraneous stimulation; therefore, the dentin-pulp complex having such morphology, regenerated by the regenerative therapeutic agent of the present invention, can also have the function possessed by the intrinsic dentin-pulp complex. It is also known that although dentin is slightly formed by a calcium hydroxide preparation, its regeneration is confined to tertiary dentin in the pulp, and the physiological morphology of the dentin-pulp complex is not configured.

The present invention also provides a method of regenerating the dentin-pulp complex, comprising a step for administering the regenerative therapeutic agent of the present invention to a subject in need thereof. Here, "a subject in need thereof" is a subject having a tooth with a dental parenchyma loss due to dental caries, tooth attrition or injury and the like, particularly a tooth with severe dental caries that reached the pulp. Subjects include not only human, but also other mammals (for example, mouse, rat, hamster, rabbit, cat, dog, cattle, sheep, monkey and the like).

The method of administering the regenerative therapeutic agent of the present invention is not particularly limited; topical administration to the exposed face of the pulp or the bottom of the dentin defect is preferable. For example, a method comprising taking an appropriate amount of the regenerative therapeutic agent of the present invention using a syringe equipped with an injection needle about 20 to 24 G thick, and administering the same to the exposed face of the pulp or the bottom of the dentin defect, and the like can be mentioned. It is also possible to administer the regenerative therapeutic agent of the present invention previously filled in the reservoir of a kit product like a simple injection device.

The dosage of the regenerative therapeutic agent of the present invention can be changed as appropriate according to the subject, severity, the subject's body weight and age, and the like, and is generally an amount that fills the exposed face of pulp or the bottom of the dentin defect, in the case of a human. Frequency of administration varies depending on the case and the dosage per treatment, and is generally about 1 to 2 times.

The present invention also provides a commercial package comprising the regenerative therapeutic agent of the present invention and a written matter. The written matter bears the statement that the regenerative therapeutic agent of the present invention can or should be used, for the treatment of regenerating the dentin-pulp complex.

Administration of the regenerative therapeutic agent of the present invention to a defect of the dentin-pulp complex or to a defect of dentin causes hard tissue formation covering the defect and remarkable neogenesis of blood vessels, as is evident from Example 1 below. As is evident from Example 2, administration to a defect of dentin without pulp exposure causes neogenesis of dentin (tertiary dentin) that retains the morphology of the dentin-pulp complex. Accordingly, the present invention provides a pulp-capping agent comprising basic fibroblast growth factor and/or a homolog thereof as an active ingredient.

Here, "pulp capping" means direct pulp capping and indirect pulp capping. "Direct pulp capping" refers to protecting an exposed non-infected pulp to promote the pulp's capability of hard tissue formation, in an attempt to close the exposed portion; "indirect pulp capping" refers to capping healthy cavity bottom dentin having become thinner due to softened dentin or cavitation due to deep dental caries and the like to protect the pulp against physicochemical stimulation and infections, and to promote the formation of repaired dentin (tertiary dentin).

bFGF and/or a homolog thereof contained in the pulp-capping agent of the present invention as an active ingredient may be the same as that contained in the regenerative therapeutic agent of the present invention.

The concentration of bFGF and/or a homolog thereof contained in the pulp-capping agent of the present invention is not particularly limited; for example, the concentration is generally 0.0001 to 20% by weight, preferably 0.001 to 10% by weight, more preferably 0.01 to 1% by weight, still more preferably 0.05 to 0.5% by weight based on the total weight of the pulp-capping agent.

The pulp-capping agent of the present invention has the excellent action of regenerating the dentin-pulp complex with a more physiological morphology and function, compared with conventionally used calcium hydroxide preparations, and can suitably be used as a pulp-capping agent for protecting the pulp of a tooth with a dental parenchyma loss due to dental caries, tooth attrition or injury and the like in the dentin-pulp complex.

The present invention also provides a method of capping pulp directly or indirectly, comprising a step for administering the pulp-capping agent of the present invention to a subject in need thereof. The subject, the method of administration and the like are the same as those for the regenerative therapeutic agent of the present invention.

The dosage of the pulp-capping agent of the present invention can be changed as appropriate according to the subject, severity, the subject's body weight and age, and the like, and is generally an amount that fills the exposed face of the pulp or the bottom of the dentin defect, in the case of a human. Frequency of administration varies depending on the case and the dosage per treatment, and is normally about 1 to 2 times.

The present invention also provides a commercial package comprising the pulp-capping agent of the present invention and a written matter. The written matter bears the statement that the pulp-capping agent of the present invention can or should be used, for direct or indirect pulp capping.

The disclosures in all publications mentioned herein, including patent application specifications, are incorporated by reference herein in the present invention to the extent that all of them have been given expressly.

EXAMPLES

The present invention is hereinafter described in detail by means of the following Examples, which are not to be construed as limitative.

Example 1

(Methods)

A preparation comprising hydroxypropylcellulose HPC; (produced by Nippon Soda Co., Ltd.) as the base and 0.089% by weight bFGF (produced by Kaken Pharmaceutical Co., Ltd.) or a preparation comprising crosslinked gelatin gel as the base and 0.4% by weight bFGF (produced by Kaken Pharmaceutical Co., Ltd.), and a preparation comprising crosslinked gelatin gel as the base and Dycal ($Ca(OH)_2$ preparation produced by Calk) were supplied for experiments. These preparations were produced by methods described in WO03/082321 and WO94/27630.

Used for animal experimentation were 1-year-old female beagle dogs. Under intravenous anesthesia with Ketalar and Nembutal, a cavity was formed on the labial face of each canine tooth in the upper and lower jaws using a diamond bar, and the tooth was drilled using a ½ round bar to expose the pulp. The operative site was washed with physiological saline, and hemostasis and drying were performed, after which each preparation was added to the exposed face of the pulp, and the cavity was filled with photopolymerizable resin after primer bonding treatment. For negative control, a tooth was not treated or treated with the base alone. After the treatment, the animals were reared on an ordinary food; 1 month later, teeth were extracted. The extracted teeth were fixed with buffered 4% paraformaldehyde solution, and decalcified with formate/sodium citrate decalcifying liquid, after which histological sections were prepared by a conventional method and stained with HE, and the effect of bFGF on the regeneration of the dentin-pulp complex was determined histopathologically.

(Results)

Using a preparation comprising crosslinked gelatin gel as the base, the effect of bFGF on dentinogenesis was determined (FIG. 1). The determination was performed in five grades with tertiary dentinogenesis as the index (−: no tertiary dentin formed, ±: almost no tertiary dentin formed, +: a small amount of tertiary dentin formed, 2+: a moderate amount of tertiary dentin formed, 3+: tertiary dentin formed remarkably). Without treatment, tertiary dentinogenesis was observed in 45%, but the extent of formation was about + in most cases. With Dycal treatment, tertiary dentinogenesis was observed only in 21.4%. However, with bFGF treatment, dentin neogenesis occurred in 50%, with the rating 2+ or 3+ obtained for all cases; remarkable dentinogenesis was observed. In summary, the bFGF treatment tended to produce clearly observable formation of tertiary dentin. When HPC was used as the base, similar results were obtained (data not shown).

With the preparation comprising crosslinked gelatin gel as the base, regeneration of the dentin-pulp complex was examined using a light microscope (×20) (FIG. 2(A)-2(D)). Without treatment, no hard tissue was formed, and vasodilation was observed in pulp tissue (FIG. 2(A)). With treatment using crosslinked gelatin gel alone, only slight hard tissue formation and signs of vasodilation were observed (FIG. 2(B)). With bFGF treatment, hard tissue formation covering the defect and remarkable neogenesis of blood vessels were observed. Also observed was remarkable formation of dentin hard tissue, and massive connective tissue formation, partially with hard tissue formation, involving deep parts of the defective dentin, was observed (FIG. 2(C)). Observed in contact with the newly formed dentin was an arrangement of odontoblast-like cells nearly identical to normal findings; regeneration of the physiological dentin-pulp complex was suggested. With Dycal treatment, a small amount of hard tissue was formed, but vasodilation and remarkable cell infiltration were observed in the pulp tissue facing the defect, showing an profile of severe inflammation (FIG. 2(D)). When HPC was used as the base, similar results were obtained (data not shown).

Figure 3:
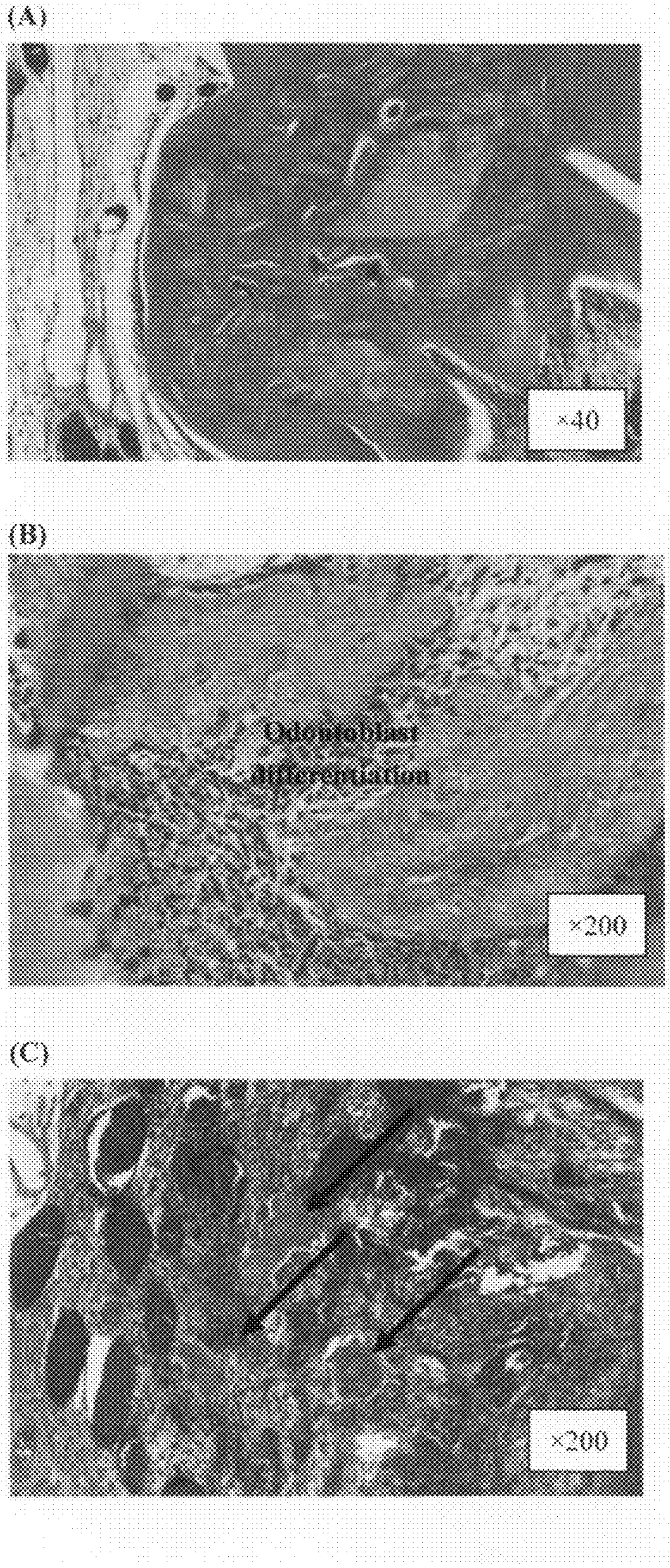
FIG. 3(A)-3(C) shows highly magnified light photomicrographs of (A) and (B) specimens treated with bFGF and (C) a specimen treated with Dycal, after HE staining, in a regeneration test for the dentin-pulp complex after pulp exposure surgery on a dog. The arrows in (C) indicate dentin formed in the pulp.

With the preparation comprising crosslinked gelatin gel as the base, regeneration of the dentin-pulp complex was examined using a light microscope at high magnification (FIG. 3(A)-(C)). With bFGF treatment, hard tissue formation was remarkable (FIG. 3(A) (×40)), and differentiation into dentin was observed (FIG. 3(B) (×200)). With Dycal treatment, the amount of hard tissue formed was small (FIG. 3(C) (×200)). When HPC was used as the base, similar results were obtained (data not shown).

Example 2

(Methods)

A preparation comprising hydroxypropylcellulose (HPC; produced by Nippon Soda Co., Ltd.) as the base and 0.089% by weight bFGF (produced by Kaken Pharmaceutical Co., Ltd.) was subjected to experiments. Animal experimentations were performed in the same manner as in Example 1, in which the pulp was not exposed in forming a dentin defect and each preparation was added to the bottom of the dentin defect. A regenerative effect of bFGF on the dentin-pulp complex free of pulp exposure was examined.

(Results)

Figure 4:
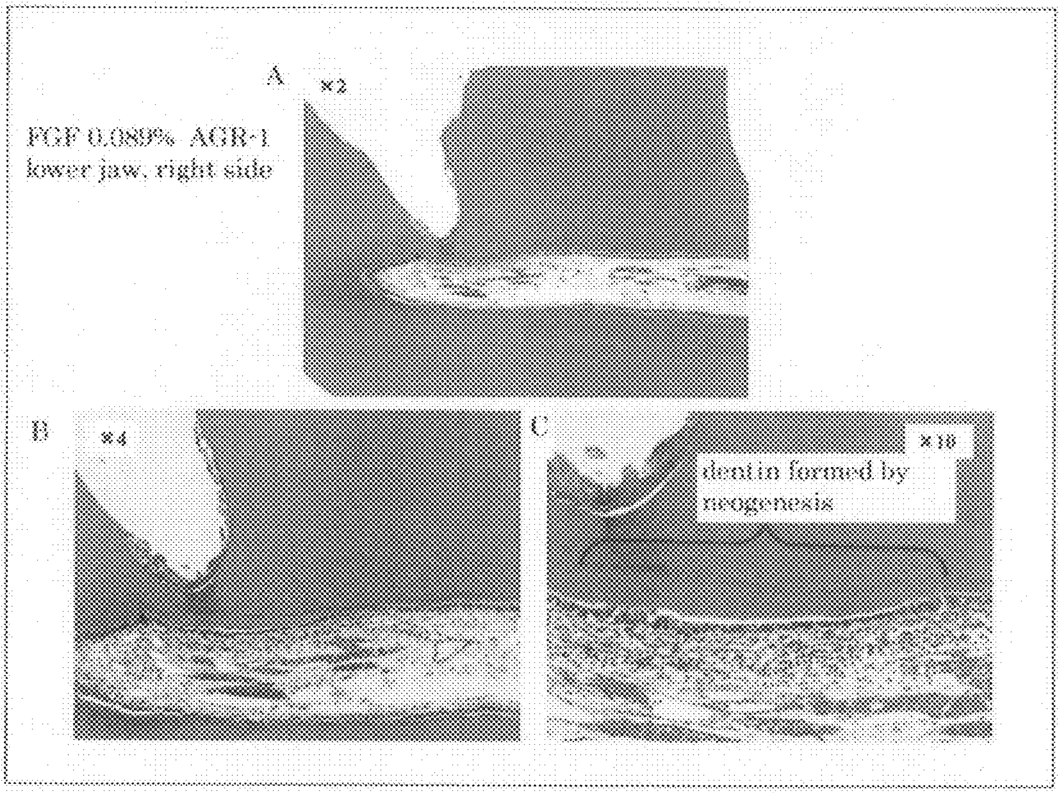
FIG. 4(A)-(C) shows a light photomicrograph of a specimen treated with bFGF, after HE staining, in a regeneration test for the dentin-pulp complex after surgery for a dentin defect without pulp exposure in a dog. (A) shows a two-fold magnification (×2), (B) shows a four-fold magnification (×4), and (C) shows a ten-fold magnification (×10).

As in Example 1, even without pulp exposure, the bFGF treatment produced dentin neogenesis retaining the morphology of the dentin-pulp complex (tertiary dentin) (FIG. 4(A)-4(C)).

INDUSTRIAL APPLICABILITY

The regenerative therapeutic agent of the present invention is effective in induction of pulp cell proliferation, pulp tissue regeneration, proliferation of odontoblast and induction of differentiation, and dentin regeneration (tertiary dentin). In the treatment of a tooth with severe dental caries, for which regenerative healing has conventionally been unexpectable, applying the regenerative therapeutic agent of the present invention makes it possible to regenerate the dentin-pulp complex, resulting in the expectation of the ideal treatment of a tooth with dental caries restoring masticatory function and perception. The dentin-pulp complex regenerated by the regenerative therapeutic agent of the present invention is capable of maintaining tooth strength, dental caries resistance, aesthetic quality, adhesiveness and the like. As a result, the method employing this therapeutic agent dramatically extends the life of permanent teeth.

Since the regenerative therapeutic agent of the present invention is capable of regenerating the dentin-pulp complex having the physiological morphology and/or function, it can serve as a therapeutic agent for dental caries that restores masticatory function and perception. As the pulp-capping agent of the present invention is also capable of regenerating the dentin-pulp complex having a nearly physiological morphology and/or function, it can suitably be used as a pulp-capping agent for protecting the pulp of a tooth with a dental parenchyma loss due to dental caries, tooth attrition or injury and the like.

This application is based on a patent application No. 2005-305076 filed in Japan (filing date: Oct. 19, 2005), the contents of which are incorporated in full herein by this reference.

The invention claimed is:

1. A method of regenerating a dentin-pulp complex, comprising a step for topically administering basic fibroblast growth factor and/or a homolog thereof in an amount sufficient to regenerate the dentin-pulp complex to an exposed face of a pulp or a bottom of a dentin defect in a subject in need thereof, wherein the dentin-pulp complex with a physiological morphology is regenerated.

2. The method of claim 1, wherein the basic fibroblast growth factor is human basic fibroblast growth factor.

3. The method of claim 1, wherein the basic fibroblast growth factor and/or a homolog thereof and a carrier are administered.

4. The method of claim 3, wherein the carrier is hydroxypropylcellulose or a crosslinked gelatin gel.

5. The method of claim 1, wherein the subject is a patient having a tooth with a dental parenchyma loss due to dental caries, tooth attrition or injury.

6. The method of claim 5, wherein the dental caries has reached the pulp.

7. A method of capping pulp directly, comprising a step for topically administering basic fibroblast growth factor and/or a homolog thereof in an amount sufficient to regenerate a dentin-pulp complex with a physiological morphology directly to an exposed face of the pulp in a subject in need thereof, wherein the pulp's capability of hard tissue formation is promoted and the exposed face of the pulp is closed.

8. The method of claim 7, wherein the basic fibroblast growth factor is human basic fibroblast growth factor.

9. The method of claim 7, wherein the basic fibroblast growth factor and/or a homolog thereof and a carrier are administered.

10. The method of claim 9, wherein the carrier is hydroxypropylcellulose or a crosslinked gelatin gel.

11. A method of capping pulp indirectly, comprising a step for topically administering basic fibroblast growth factor and/or a homolog thereof in an amount sufficient to induce neogenesis of a dentin-pulp complex with a physiological morphology indirectly to a bottom of a dentin defect in a subject in need thereof, wherein the formation of repaired dentin is promoted.

12. The method of claim 11, wherein the basic fibroblast growth factor is human basic fibroblast growth factor.

13. The method of claim 11, wherein the basic fibroblast growth factor and/or a homolog thereof and a carrier are administered.

14. The method of claim 13, wherein the carrier is hydroxypropylcellulose or a crosslinked gelatin gel.

* * * * *